(12) United States Patent
Mehldau

(10) Patent No.: US 6,865,249 B2
(45) Date of Patent: Mar. 8, 2005

(54) METHOD FOR OPERATING A COMPUTED TOMOGRAPHY APPARATUS

(75) Inventor: Heiko Mehldau, Nuremberg (DE)

(73) Assignee: Siemens Aktiengesellschaft, Münich (DE)

(*) Notice: Subject to any disclaimer, the term of this patent is extended or adjusted under 35 U.S.C. 154(b) by 143 days.

(21) Appl. No.: 10/135,429

(22) Filed: Apr. 30, 2002

(65) Prior Publication Data

US 2002/0181646 A1 Dec. 5, 2002

(30) Foreign Application Priority Data

May 31, 2001 (DE) .......................................... 101 26 641

(51) Int. Cl.[7] .................................................. A61B 6/00
(52) U.S. Cl. .................................. 378/8; 378/4; 378/21
(58) Field of Search ............................ 378/4, 8, 15, 21, 378/901; 382/131, 132, 291, 294; 600/408, 409, 425

(56) References Cited

U.S. PATENT DOCUMENTS

| | | | |
|---|---|---|---|
| 5,315,628 A | 5/1994 | Guendel | 378/20 |
| 6,173,033 B1 | 1/2001 | Klingenbeck-Regn et al. | 378/20 |
| 6,501,819 B2 * | 12/2002 | Unger et al. | 378/5 |
| 6,512,808 B2 * | 1/2003 | Klingenbeck-Regn | 378/18 |

* cited by examiner

*Primary Examiner*—Edward J. Glick
*Assistant Examiner*—Courtney Thomas
(74) *Attorney, Agent, or Firm*—Schiff Hardin LLP

(57) ABSTRACT

In a method for operating a computed tomography apparatus, a topogram of a region of a subject, for which a volume dataset is to be obtained by computed tomography, is obtained and the image data of the topogram are analyzed to obtain an analysis result. The analysis result can be used for mixing a marking into the topogram for defining the region for which the volume dataset is to be obtained, or the analysis result can be used to align and operate a gantry of the computed tomography apparatus for obtaining the volume dataset. Manual determination and entry of the marking and/or manual control of the gantry, are thus avoided.

18 Claims, 5 Drawing Sheets

METHOD FOR OPERATING A COMPUTED TOMOGRAPHY APPARATUS

BACKGROUND OF THE INVENTION

1. Field of the Invention

The present invention is directed to a method for operating a computed tomography apparatus with which a region of a life form, for which a volume dataset of the life form is to be registered, is determined.

2. Description of the Prior Art

Before the definition of the region for which a volume dataset is to be registered, for example by means of a spiral scan, an x-ray shadowgram (topogram) of the life form is usually produced. The definition of the region for which the volume dataset is to be registered ensues by means of a graphic marking of a region, that is generally a rectangular region in the topogram, that includes the region of the life form to be registered. The length of the rectangle defines the length of the spiral scan and the width of the rectangle defines the width of the field of view presented in the CT image.

So that the x-ray topogram covers as few regions as possible that are not allocated to the region to be registered, German PS 42 23 430 teaches that the x-ray topogram be generated keeping pace with the measurement. The x-ray topogram is generated in real time by a computer of the computed tomography apparatus using the output signals of the detector array of the computed tomography apparatus, acquired in real time, to generate an x-ray topogram that corresponds to the degree of the relative position between a measurement unit, including the detector array and the x-ray source, and the patient bed of the computed tomography apparatus.

When the radiation detector has more than one detector array, i.e. when the radiation detector is a matrix detector, it can occur that the matrix detector covers the entire examination region for which the x-ray topogram is to be registered. In this case, the measurement unit formed by the matrix detector and the x-ray source need not move relative to the patient bed. In this context, German OS 197 21 535 discloses a computed tomography apparatus having a matrix detector with which x-ray topograms can be optionally prepared using one or more detector lines. To this end, a tube-proximate slotted diaphragm and a detector-proximate slotted diaphragm are provided. An on-line computing method is employed for the superimposition of the x-ray topograms of the individual detector lines, this including a "deblurring filter" for reduction of the image blurring due to the movement of the patient bed and including correction for stray radiation in the matrix detector.

The marking is manually defined by an operator of the computed tomography apparatus, as a result of which the region for which the volume dataset is to be registered can be relatively imprecisely marked on occasion. The manual setting of this marking is also relatively time-consuming.

SUMMARY OF THE INVENTION

It is an object of the invention to provide a method that creates pre-requisites for an easier determination of that region for which the volume dataset is to be registered.

According to the invention, this object is achieved in a method for determining a position and size of a marking that is mixed into a topogram of a living subject registered with a computed tomography apparatus and defines that region of the subject for which a volume dataset of the subject is to be registered, comprising the following method steps:

a) Producing the topogram,
b) Analyzing the image data allocated to the topogram, and
c) Mixing in the marking based on the analysis.

In accordance with the invention, thus, the operator of the computed tomography apparatus need not manually enter the position and size of the marking that limits the region for which the volume dataset is to be registered into the topogram. Instead, this region is mixed into the topogram on the basis of the analysis of the image data allocated to the topogram. The marking can, for example, be determined with a suitable computer program of a control computer of the computed tomography apparatus and, in particular, can be automatically mixed into the topogram. After the marking has been mixed into the topogram, a gantry of the computed tomography apparatus is aligned and operated in a well known way so that the region for which the volume dataset is to be registered is scanned. A manual step in the examination of the subject with the computed tomography apparatus is thus eliminated, so that a faster and more precise examination of the subject is enabled.

The object of the invention also is achieved in a method for determining a region of a living subject for which a volume dataset of the subject is to be registered, comprising the following method steps:

a) Producing a topogram of the life form,
b) Analyzing the image data allocated to the topogram, and
c) Based on the analysis, aligning and operating a gantry of the computed tomography apparatus such that the volume dataset is registered over the entire region.

Similar to the inventive method set forth above, thus, a topogram of the subject is inventively registered and the image data allocated to the topogram are analyzed. Instead of determining a marking that is mixed into the topogram and defines that region for which the volume dataset is to be registered, the gantry is already inventively aligned and operated such that the region for which the volume dataset is to be registered is covered. Compared to known systems and methods, a manual step is again eliminated in the examination of the subject with the computed tomography apparatus.

The gantry can be operated during the scanning of the subject for registering the volume dataset so that the region for which the volume dataset is to be registered is exactly covered. In the scanning, however, a small safety margin can be included, so that it is assured that the entire region for which the volume dataset is to be registered is in fact covered.

Since often only the torso of the subject is examined, the topogram according to a version of the invention is a topogram of the torso of the subject. Further, only the thorax, the abdomen or the pelvis of the life form is often of interest in an examination. Consequently, in an embodiment of the invention the region of the subject for which the volume dataset is to be registered is the thorax, the abdomen and/or the pelvis of the life form.

Another typical examination with a computed tomography apparatus is a head examination. According to a further version of the invention, thus, the topogram is a lateral topogram of the head of the subject. In the head examination, either a volume dataset of the base of the skull or of the cerebrum is usually required. In another embodiment of the invention the region of the subject for which the volume dataset is to be registered is the base of the skull and/or the cerebrum. When registering the volume dataset, further, the gantry of the computed tomography apparatus is suitably inclined in relation to the angle of the base of the skull during the head examination. In one version of the invention, the angle of the base of the skull of the head is therefore defined based on the analysis of the image data allocated to the topogram in order to incline the gantry of the computed tomography apparatus in a suitable way during the registration of the volume dataset.

In a preferred embodiment of the invention, a pattern recognition unit is employed for the analysis of the image data allocated to the topogram. The pattern recognition unit can include a neural network according to a preferred version of the invention.

In another embodiment of the invention, the data allocated to the topogram are compared to a semantic model of a subject during the course of the analysis.

DESCRIPTION OF THE PREFERRED EMBODIMENTS

Figure 1:
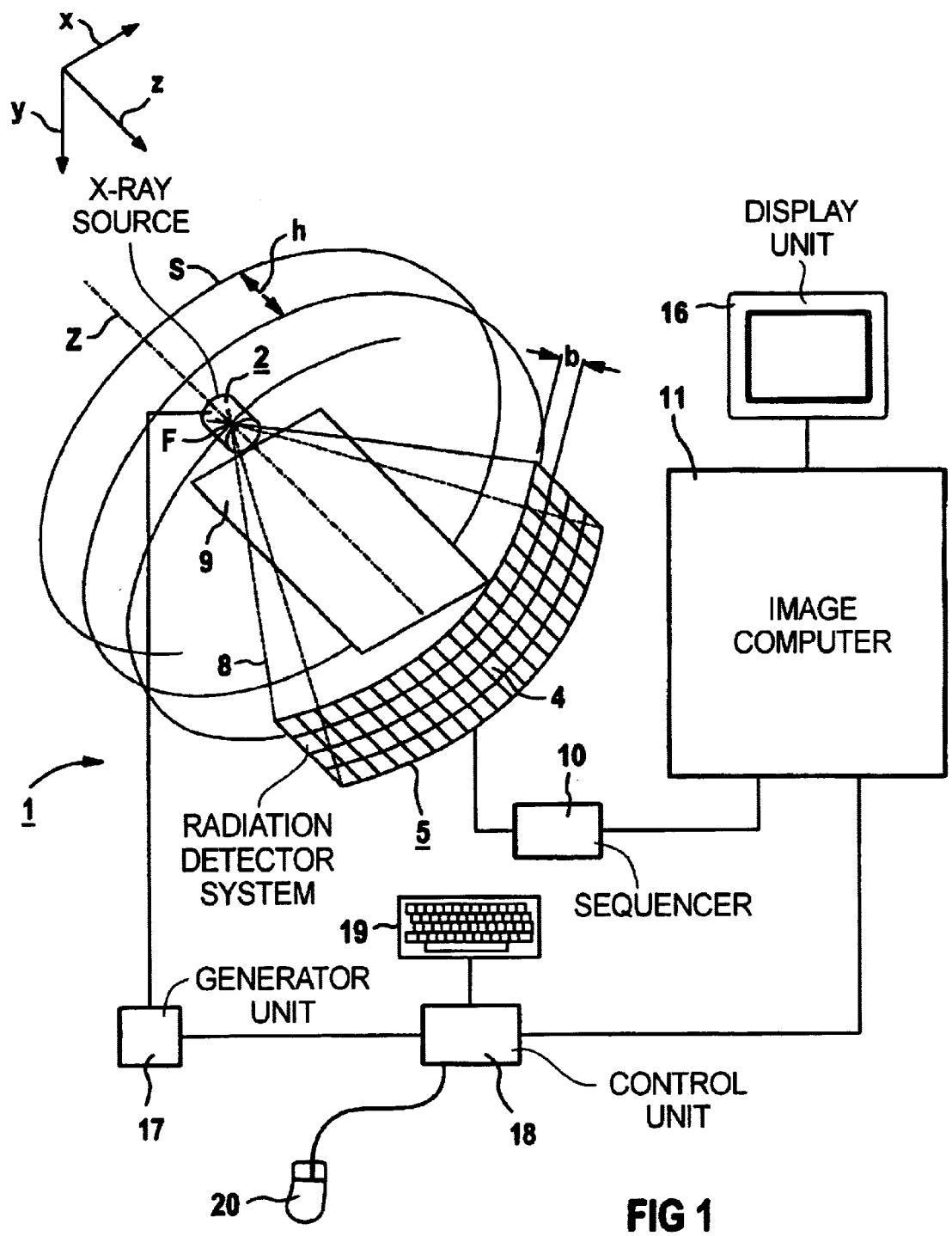
FIG. 1 is a schematic illustration of a computed tomography apparatus suitable for the implementation of the inventive methods, partially in perspective, partially in the fashion of a block diagram.
Figure 2:
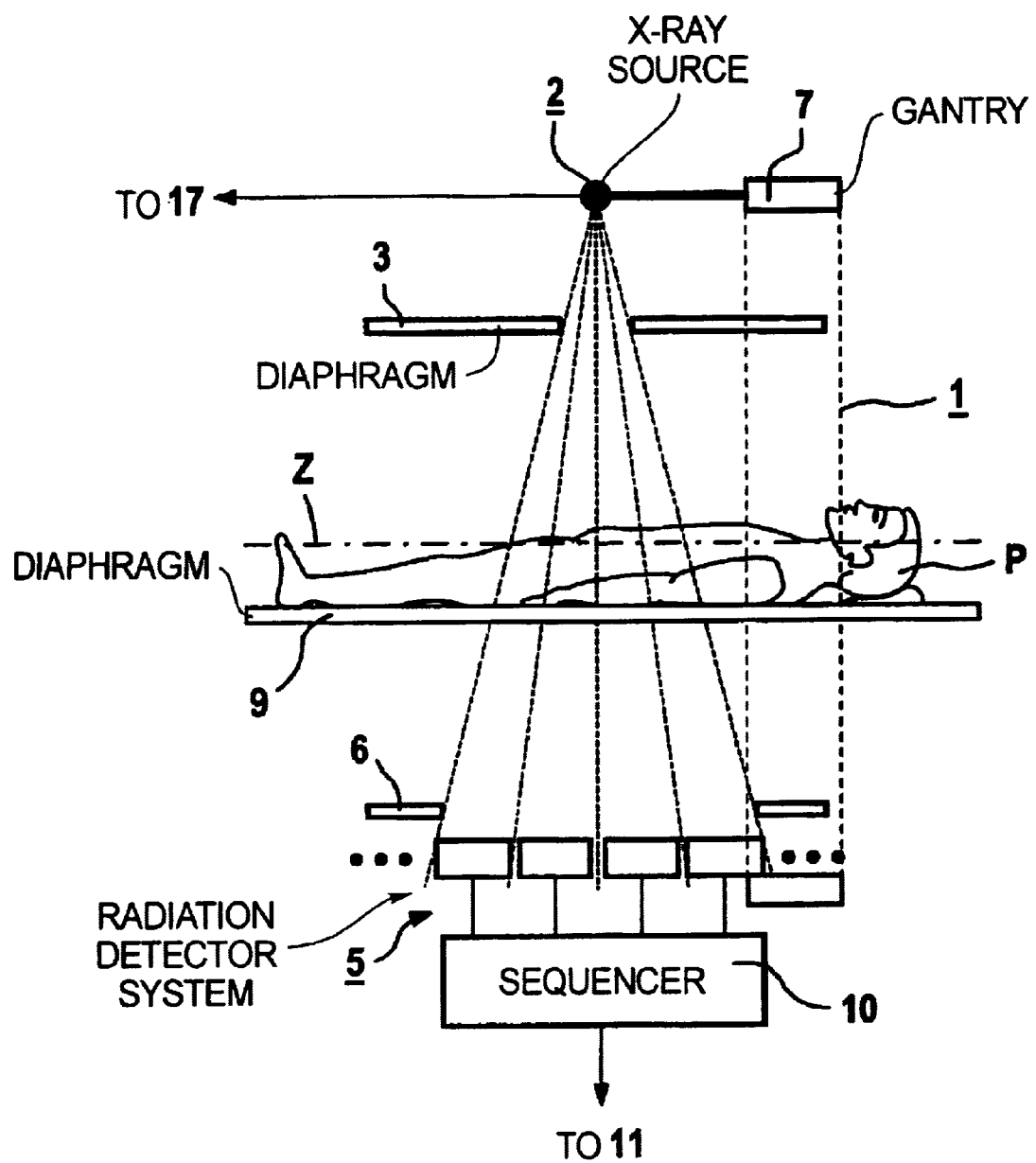
FIG. 2 is a longitudinal section through the computed tomography apparatus according to FIG. 1.

FIGS. 1 and 2 show a computed tomography apparatus of the third generation suitable for the implementation of the inventive method. The measurement arrangement 1 thereof includes an x-ray source 2 having a source-proximate radiation diaphragm 3 (FIG. 2) placed in front of it and having a radiation detector system 5. The detector system 3 is fashioned as a planar array of a number of rows and columns of detector elements—one of these is referenced 4 in FIG. 1—with a detector-proximate radiation diaphragm 6 (FIG. 2) placed in front of it. The x-ray source 2 with the radiation diaphragm 3, and the detector system 5 with the radiation diaphragm 6, are mounted opposite one another on a live frame (gantry) 7 as shown in FIG. 2 such that a pyramidal x-ray beam that emanates from the x-ray source 2 during operation of the computed tomography apparatus and that is gated by the adjustable radiation diaphragm 3, and whose edge rays are referenced 8, strikes the detector system 5. The radiation diaphragm 6 is set, dependent on the cross-section of the x-ray beam set with the radiation diaphragm 3 so that only that region of the detector 5 is enabled that can be immediately struck by the x-ray beam. In the operating mode shown in FIGS. 1 and 2, these are four rows of detector elements. The fact that other rows of detector elements covered by the radiation diaphragm 6 are present is indicated dotted in FIG. 2.

Using a drive device (not shown), the gantry 7 can be placed in rotation around a system axis Z. The system axis Z proceeds parallel to the z-axis of a spatial rectangular coordinate system shown in FIG. 1.

The columns of the detector system 5 likewise proceed in the direction of the z-axis, and the rows, whose width b is measured in the direction of the z-axis and, for example, amounts to 1 mm, proceed transversely relative to the system axis Z, or to the z-axis.

In order to be able to place a patient P shown in FIG. 2 into the beam path of the x-ray beam, a support mechanism 9 is provided that is displaceable parallel to the system axis Z, i.e. in the direction of the z-axis.

A scanning ensues for registering a volume dataset of the patient P wherein a number of projections are registered from different projection directions upon movement of the measurement unit 1 around the system axis Z. The data supplied by the detector system 5 thus contain a number of projections.

During the continuous rotation of the measurement unit 1 around the system axis Z, the support mechanism 9 is simultaneously continuously displaced in the direction of the system axis Z relative to the measurement unit 1. A synchronization between the rotational movement of the gantry 7 and the translational movement of the support mechanism 9 is present in the sense that the relationship of translational to rotational velocity is constant. This constant relationship can be set by selecting a value assuring a complete scanning of the region of interest of the patient P for the feed h of the support mechanism 9 per revolution of the gantry 7. As viewed from the patient P, the focus F of the x-ray source 2 moves around the system axis Z on a helical spiral path referenced S in FIG. 1, for which reason the described type of exposure of the volume dataset is also referred to as spiral scan. The volume data thereby supplied by the detector elements of each row of the detector system 5 represent projections respectively allocated to specific rows of the detector system 5 and a specific position with respect to the system axis Z. The data are read out in parallel, are serialized in a sequencer 10 and are transmitted to an image computer 11.

The volume data are pre-processed in the image computer 11. The data stream resulting therefrom subsequently proceeds to a memory of the image computer 11 wherein the volume data corresponding to the data stream are stored.

The image computer 11 also includes a reconstruction unit that reconstructs image data, for example in the form of tomograms of desired slices of the patient P, from the volume data according to methods known to those skilled in the art. The image data reconstructed by the reconstruction unit are stored in the memory of the image computer 11 and can be displayed on a display unit 16, for example a video monitor, connected to the image computer 11.

The x-ray source 2 for example an x-ray tube, is supplied with the necessary voltages and currents by a generator unit 17. In order to be able to set these to the values needed for a particular scan, the generator unit 17 has a control unit 18 with keyboard 19 and mouse 20 allocated to it that allows the necessary settings to be undertaken.

The rest of the operation and control of the computed tomography apparatus also ensues with the control unit 18 and the keyboard 19 as well as the mouse 20, this being illustrated in that the control unit 18 is connected to the image computer 11.

In order to restrict the registration of volume data to the diagnostically necessary region and, thus, to save the patient P from unnecessary exposure to radiation, a topogram of the diagnostically relevant region of the patient P is prepared before the registration of the volume data. With an activated x-ray source 2 but without rotation of the measurement unit 1 around the system axis Z, a displacement of the support mechanism 6 in the direction of the system axis 7 relative to the measurement unit 1 is implemented, with the x-ray source 2 activated as necessary for the acquisition of the diagnostically relevant region of the patient P. The output data of the detector system 5 that thereby arise are transmitted in serial form to the image computer 11 that calculates a topogram from the data according to known algorithms, presents this topogram on the display unit 16 and, if desired, stores it in the memory of the image computer 11.

Figure 3:
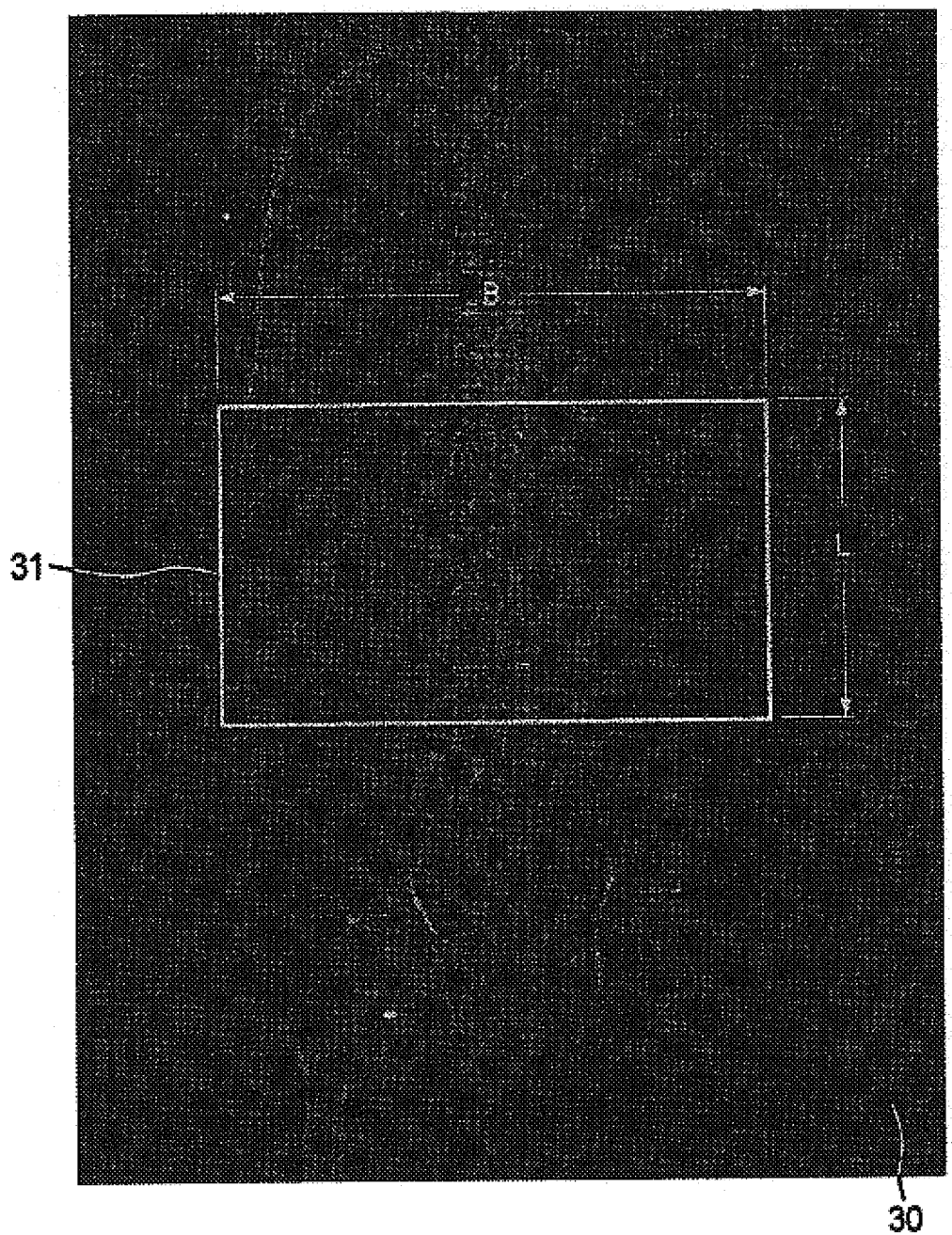
FIG. 3 is a topogram of the torso of a patient examined with the computed tomography apparatus shown in FIGS. 1 and 2 in accordance with the invention.

FIG. 3 shows a topogram 30 as an example that is a topogram 30 of the torso of the patient P in the exemplary embodiment. When a topogram of the torso of a patient is registered, either a volume dataset of the thorax, of the abdomen or of the pelvis of the patient is usually to be registered.

Figure 4:
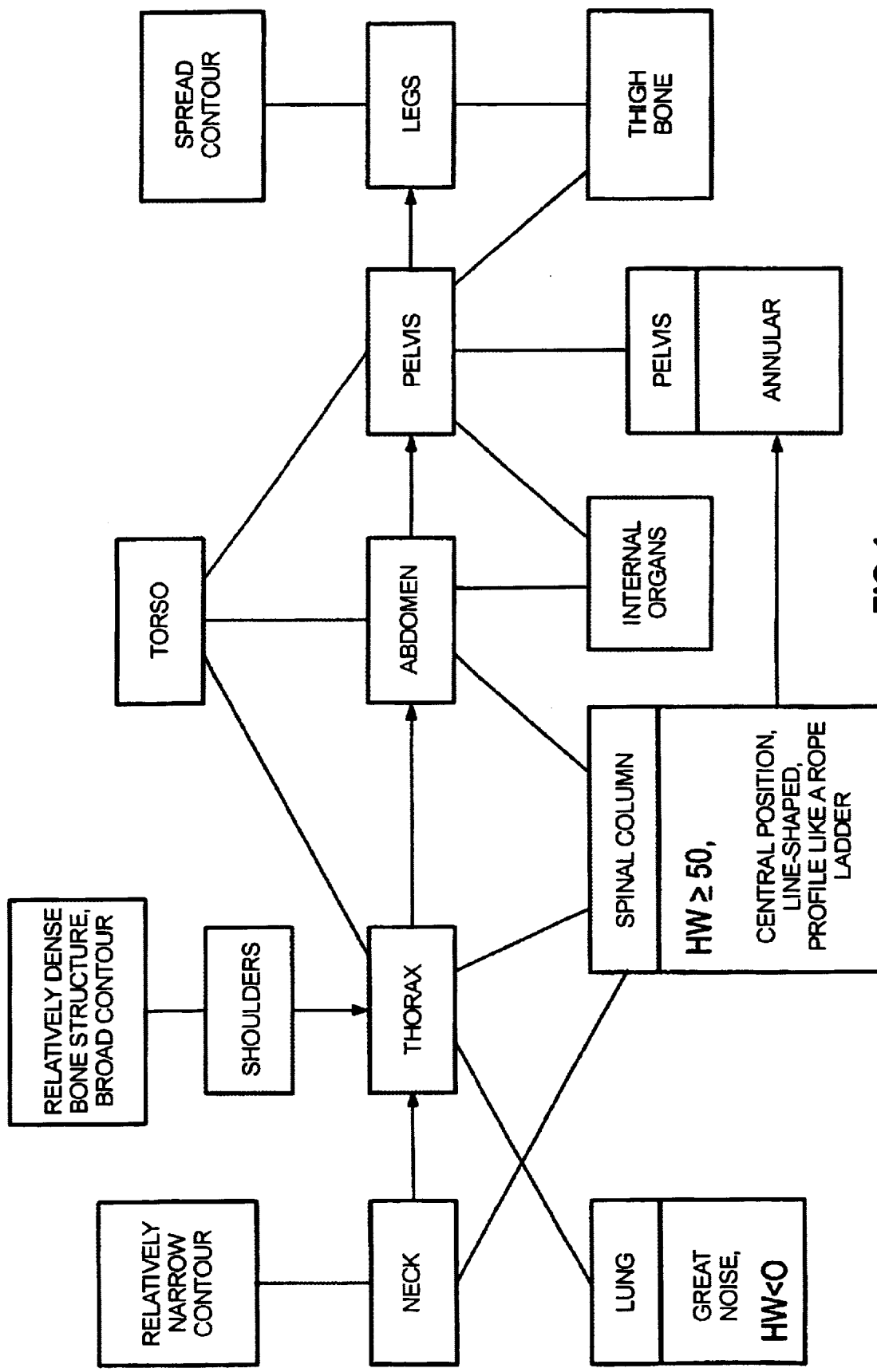
FIG. 4 is a semantic model of a human.

In order to then correspondingly allocate these regions to the topogram 30, a computer program stored in the image computer 11 of the computed tomography apparatus 1 analyzes the image data allocated to the topogram 30 with a pattern recognition unit in a first operating mode. In particular, thus, the degree of attenuation of the x-rays or the contours of the topogram 30 allocated to the image data are analyzed. Using a neural network, it is particularly the position of internal organs, of the spinal column, of the legs, etc., that are determined. The analysis acquired in this way is subsequently compared to a semantic model of a human that is likewise stored in the image computer 11 and is shown as an example in FIG. 4. The semantic model is constructed such that various regions of the human are defined and described, so that the position of the regions thorax, abdomen and pelvis in the topogram 30 of the patient P can be defined on the basis of the comparison of the semantic model to the analysis of the image data. The semantic model is constructed in the following way.

The torso comprises the thorax, the abdomen and the pelvis. Further regions that can be at least partially imaged on a topogram of the torso of the patient P are at least parts of the neck of the shoulders and of the legs. Compared to the torso, the neck particularly exhibits a narrow contour and adjoins the shoulders. The shoulders have a relatively dense bone structure, which results in a relatively strong attenuation of the x-ray beam emanating from the x-ray source 2. The shoulders also exhibit a relatively broad contour.

The thorax adjoins the next neck and the shoulders. The thorax comprises the lungs that, due to a mixture of air and tissue, exhibits relatively high noise and a Hounsfield width (HW) less than 0. The Hounsfield width is a criterion for the attenuation of the x-rays. Further, the thorax comprises the spinal column that exhibits a Hounsfield width greater than or equal to 50, is fashioned line-like and is approximately centrally arranged and exhibits a profile shaped like a lope ladder. The projection of the spinal column in a topogram of the torso also proceeds through the projection of the lung.

The abdomen adjoins the thorax. The abdomen likewise comprises the spinal column. It also comprises internal organs.

The pelvis adjoins the abdomen. It comprises at least parts of the internal organs, parts of the thigh bones and an approximately annular pelvis. The projection of the pelvis in a topogram of the torso, further, adjoins the projection of the spinal column.

Two legs are adjacent to the pelvis, comprising the thigh bones and exhibiting a divided contour.

After the computer program stored in the image computer 11 has defined the position and size of the regions of thorax, abdomen and pelvis in the topogram 30, an operator (not shown in FIGS. 1 and 2) can decide with the keyboard 19 or the mouse 20 whether a volume dataset of the patient P should be registered that covers the thorax, the abdomen or the pelvis. After the selection of the region for which the volume dataset is to be registered and after this region has been identified by the above-described method, a rectangular mark 31 that bound the selected region is mixed into the topogram 30. In the exemplary embodiment, the operator would like to register a volume dataset of the abdomen of the patient P, for which reason a rectangular mark 31 that bounds the abdomen is mixed into the topogram P. Before the volume dataset is registered, the operator can check the position and size of the mark 31 and corrected if necessary.

On the basis of the position and size of the mark 31 that has been mixed in, the gantry 7 of the computed tomography apparatus is subsequently aligned and operated in a notoriously known way such that the entire region bounded by the mark 31 is scanned, i.e. a volume dataset of the abdomen of the patient P is produced. The length L of the mark 31 thereby defines the length of the scan and the width B of the mark 31 defines the width of the field of view presented in the CT image.

The computed tomography apparatus, however, can also be operated in another operating mode. In this operating mode, the computer program of the image computer 11—as set forth above—determines the regions of thorax, abdomen and pelvis. In contrast to the first operating mode, however, the gantry 7 of the computed tomography apparatus 1 is immediately aligned and operated such that the desired region of the patient P is scanned after the operator has decided whether a volume dataset of the thorax, of the abdomen or of the pelvis is to be registered. The step wherein a mark 31 is mixed into the topogram 30 is thus eliminated. A display of the topogram 30 with the display unit 16 is also unnecessary in this operating mode.

Figure 5:
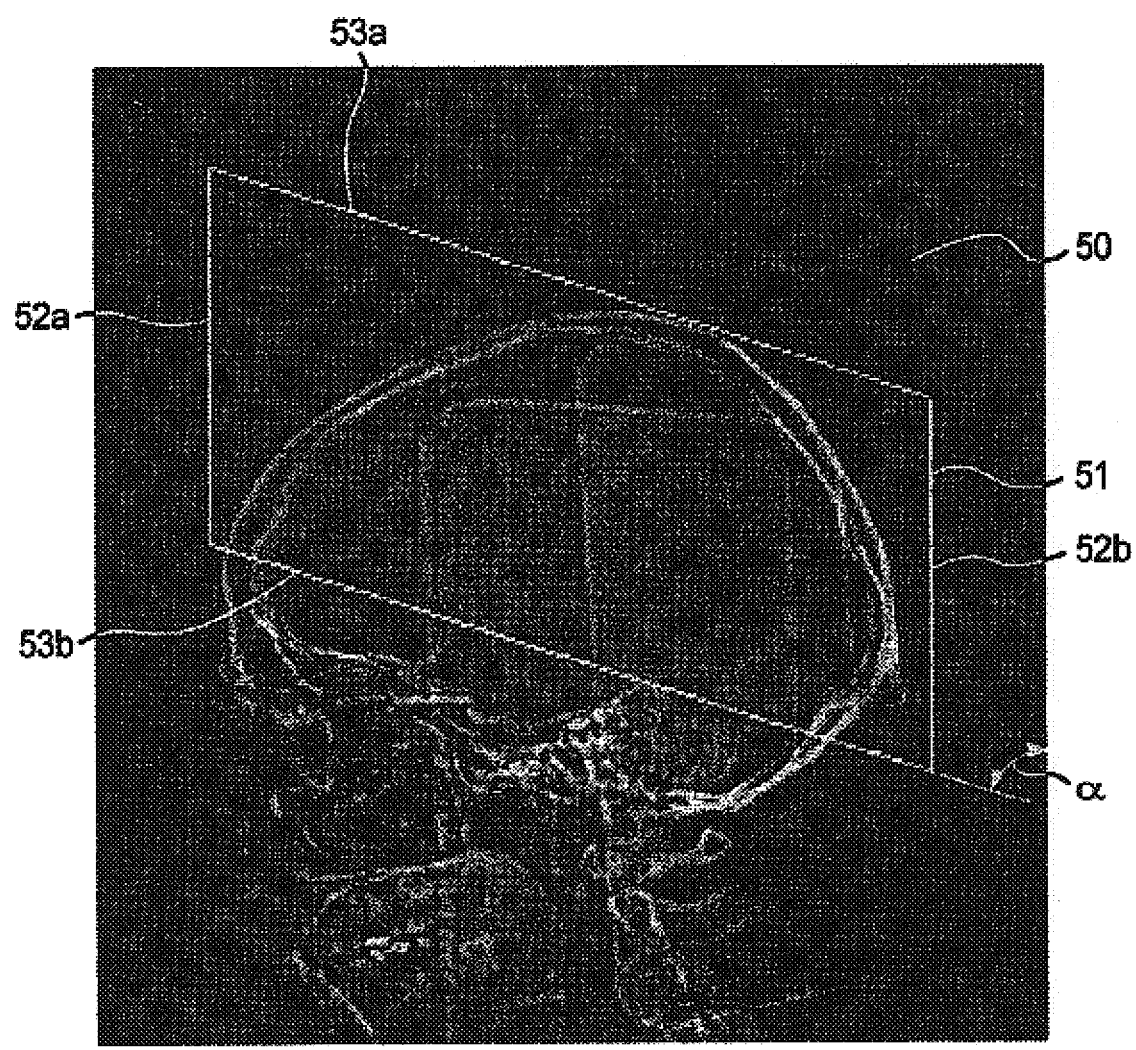
FIG. 5 is a lateral topogram of the head of the patient obtained in accordance with the invention.

FIG. 5 shows another example of a topogram 50 that, in the case of the exemplary embodiment, is a lateral topogram 50 of the head of the patient P that was registered during a head examination of the patient P. In a head examination, one would usually like to register either a volume dataset of the base of the skull or of the cerebrum. During the registration of the volume dataset, further, the gantry 7 of the computed tomography apparatus is usually inclined by the angle of the base of the skull that is defined by the position of the base of the skull and of the patient bed 9.

In order to identify the region for which the volume dataset is to be registered, a computer program stored in the image computer 11 analyzes the image data allocated to the topogram 50 in a further operating mode with means for pattern recognition, which again includes a suitably trained neural network in the exemplary embodiment, in order to determine the regions of base of the skull and cerebrum. The operator subsequently decides whether a volume dataset of the base of the skull or of the cerebrum is to be registered, whereupon a corresponding mark 51 shaped like a parallelogram is mixed into the topogram 50. In the exemplary embodiment, a volume dataset of the cerebrum is to be registered, for which reason the mark 51 outlines the cerebrum of the patient P imaged in the topogram 50.

The limiting lines 52a and 52b of the mark 51 are aligned parallel or at a right angle to the bounds of the topogram 50; the limiting lines 53a and 53b of the mark 51, in contrast, are turned by an angle a relative to the bounds of the topogram 50. The angle a corresponds to the angle of the base of the skull and was likewise determined with the computer program stored in the image computer 11 during the analysis of the image data allocated to the topogram 50.

Before the volume dataset is registered, the operator can check and potentially modify the size and position of the mark 51.

As a result of the position and size of the mixed-in mark 51 as well as of the identified angle a of the base of the skull, the gantry 7 slants such that a scanning of the head of the patient P proceeds at a right angle relative to the limiting lines 52a and 52b of the topograph 50. Further, the gantry 7 is aligned and operated such that the entire region bounded by the mark 51 is scanned, i.e. a volume dataset of the cerebrum of the head of the patient P is produced. The length of the limiting lines 52a or 52b of the mark 51 thereby defines the length of the scan and the length of the limiting lines 53a or 53b of the mark 51 defines the width of the field of view presented in the CT image.

The computed tomography apparatus 1, however, can also be operated in a further operating mode. In this operating mode, the computer program of the image computer 11—as set forth above—determines the regions of the base of the skull and cerebrum as well as the angle a of the base of the skull. In contrast to the above-described operating mode, however, the gantry 7 is immediately aligned and operated such that the desired region of the patient P is scanned after the operator has decided whether a volume dataset of the base of the skull or of the cerebrum is to be registered. The step wherein the mark 51 is mixed into the topogram 50 is thus again eliminated. A display of the topogram 50 is also again optional for this operating mode.

Although only a topogram 30 of the torso and a lateral topogram 50 of the head of the patient P have been described in the exemplary embodiment, the inventive techniques also can be employed for other topograms. The regions for which a volume dataset are to be registered are likewise only examples. In particular, these regions can also be allocated to the heart, to the stomach, to the legs, to specific internal organs, etc. of the patient P.

The semantic model shown in FIG. 3 is likewise only an example. Moreover, it is optional for the inventive method. A pattern recognition with neural network is likewise not compulsory. Other means for pattern recognition, for example based on fuzzy logic, or other analysis methods for analyzing the image data allocated to the topogram can also be employed.

The computed tomography apparatus need not necessarily be a computed tomography apparatus of the third generation.

The patient P need not necessarily be a human being, as FIGS. 2 through 5 suggest. The inventive methods can also be applied for animals.

Although modifications and changes may be suggested by those skilled in the art, it is in the intention of the inventor to embody within the patent warranted hereon all changes and modifications as reasonably and properly come within the scope of the inventors contribution to the art.

I claim as my invention:

1. A method for setting a position and size of a marking mixed into a topogram of a living subject obtained by x-ray computed by tomography, said marking defining a region of said subject for which a volume dataset of said subject is to be obtained, comprising the steps of:
    obtaining image data representing said topogram using an x-ray computed tomography apparatus with a gantry maintained stationary;
    non-manually electronically analyzing said image data of said topogram in a computer to obtain an analysis result; and
    automatically electronically mixing said marking into said topogram with a position and size dependent on said analysis result.

2. A method as claimed in claim 1 comprising obtaining said image data comprising said topogram from torso of said subject.

3. A method as claimed in claim 1 comprising mixing said marking into said topogram for obtaining said volume dataset from a region of said subject selected from the group consisting of the thorax, the abdomen and the pelvis.

4. A method as claimed in claim 1 comprising obtaining said image data to generate a lateral topogram of the head of said subject as said topogram.

5. A method as claimed in claim 1 comprising mixing said marking into said topogram for obtaining said volume dataset from a region of said subject selected from the group consisting of the base of the skull and the cerebrum.

6. A method as claimed in claim 5 wherein the step of analyzing said image data comprises analyzing said image data to identify an angle of the base of the skull of said subject to the head of said subject, as said analysis result, and further comprising inclining a gantry of a computed tomography apparatus, dependent on said angle, for obtaining said volume dataset.

7. A method as claimed in claim 1 wherein the step of analyzing said image data comprises analyzing said image data employing a pattern recognition algorithm.

8. A method as claimed in claim 7 wherein comprising executing said pattern recognition algorithm in a neural network.

9. A method as claimed in claim 1 wherein the step of analyzing said image data comprises analyzing said image data by comparison to a semantic model of said subject.

10. A method for determining a region of a living subject for which a volume dataset of a subject is to be obtained with an x-ray computed tomography apparatus having an inclinable gantry, comprising the steps of:
    obtaining image data comprising a topogram of said subject using said x-ray computed tomography apparatus with said gantry stationary;
    non-manually electronically analyzing said image data of said topogram in a computer to obtain an analysis result; and
    automatically aligning and operating said gantry in said computed tomography apparatus dependent on said analysis result for obtaining said volume dataset over an entirety of said region.

11. A method as claimed in claim 10 comprising obtaining said image data comprising said topogram from torso of said subject.

12. A method as claimed in claim 10 comprising mixing said marking into said topogram for obtaining said volume dataset from a region of said subject selected from the group consisting of the thorax, the abdomen and the pelvis.

13. A method as claimed in claim 10 comprising obtaining said image data to generate a lateral topogram of the head of said subject as said topogram.

14. A method as claimed in claim 10 comprising mixing said marking into said topogram for obtaining said volume dataset from a region of said subject selected from the group consisting of the base of the skull and the cerebrum.

15. A method as claimed in claim 10 wherein the step of analyzing said image data comprises analyzing said image data to identify an angle of the base of the skull of said subject to the head of said subject, and wherein the step of aligning and operating said gantry comprises inclining said gantry dependent on said angle.

16. A method as claimed in claim 10 wherein the step of analyzing said image data comprises analyzing said image data employing a pattern recognition algorithm.

17. A method as claimed in claim 16 wherein comprising executing said pattern recognition algorithm in a neural network.

18. A method as claimed in claim 10 wherein the step of analyzing said image data comprises analyzing said image data by comparison to a semantic model of said subject.

* * * * *